United States Patent [19]

Micheli

[11] 4,098,801

[45] Jul. 4, 1978

[54] SYNTHESIS OF 1α-HYDROXYLATED DERIVATIVES OF CHOLESTEROL

[75] Inventor: Robert Angelo Micheli, Passaic, N.J.

[73] Assignee: Hoffmann-La Roche Inc., Nutley, N.J.

[21] Appl. No.: 762,604

[22] Filed: Jan. 26, 1977

[51] Int. Cl.$^2$ .............................................. C07J 5/00
[52] U.S. Cl. ........................ 260/397.2; 260/239.55 R
[58] Field of Search ..................................... 260/397.2

[56] References Cited

U.S. PATENT DOCUMENTS

| | | | |
|---|---|---|---|
| 3,887,545 | 6/1975 | Iacobelli et al. | 260/397.2 |
| 3,901,928 | 8/1975 | Hesse et al. | 260/397.2 |

OTHER PUBLICATIONS

Pele et al. "J. Chem. Soc." 1970 © p. 1624.

*Primary Examiner*—Elbert L. Roberts
*Attorney, Agent, or Firm*—Samuel L. Welt; George M. Gould; Raymond R. Wittekind

[57] ABSTRACT

A process for the preparation of 1α-hydroxylated cholesterol derivatives useful for the synthesis of 1α-hydroxylated cholecalciferols, is disclosed.

8 Claims, No Drawings

SYNTHESIS OF 1α-HYDROXYLATED DERIVATIVES OF CHOLESTEROL

BACKGROUND OF THE INVENTION

1α-Hydroxylated cholecalciferols (vitamin D₃s), particularly 1α-hydroxycholecalciferol and 1α,25-dihydroxycholecalciferol, metabolites of cholecalciferol, are more active than the vitamin in both intestinal calcium transport and bone calcium mobilization and therefore have been extensively studied for the treatment of various vitamin D₃ deficiency diseases. Promising results have been obtained with 1α-hydroxylated cholecalciferols in the treatment of such diseases, for example, osteoporosis and renal failure. See the review article on vitamin D by J. L. Omdahl and H. F. DeLuca, Physiological Reviews, 53, 327 (1973).

The interesting biological activity exhibited by 1α-hydroxylated derivatives of cholecalciferol has stimulated very extensive chemical research activity directed toward the synthesis of 1α-hydroxylated cholesterols, which are readily converted to the 1α-hydroxylated cholecalciferols following well-trodden paths. See, for example, B. Pelc and E. Kodicek, J. Chem. Soc. (C), 1624 (1970), M. Morisaki, et al., Chem. Pharm. Bull. (Japan), 21, 1853 (1973), J. J. Rubio-Lightbourn, Chem. Pharm. Bull. (Japan), 21, 1854 (1973), D. H. R. Barton, et al., J. Am. Chem. Soc., 95, 2748 (1973) and D. H. R. Barton, et al., J.C.S. Chem. Comm., 203 (1974).

Recently, J. A. Iacobelli, et al., in U.S. Pat. No. 3,887,545, issued June 3, 1975, described a novel synthesis of 1α-hydroxylated cholesterols starting from the epoxyketone of formula I and involving the steps of reductively cleaving the epoxy group of I to the hydroxyketone of formula II, reducing the keto group of II to the diol of formula IV and eliminating the sulfonyloxy group of IV to the 1α-hydroxylated cholesterols of formula V. See Reaction Scheme I.

The use of difficultly preparable and potentially hazardous aluminum amalgam to reductively cleave the epoxyketone of formula I to the extremely labile β-ketoalcohol of formula II in the Iacobelli scheme, while of no serious consequence when the synthesis is performed on a laboratory scale, detracts from its efficiency and practicality when the synthesis is scaled-up to, for example, pilot plant levels. Thus a synthesis of 1α-hydroxylated cholesterols avoiding the use of aluminum amalgam and the formation of the labile intermediate β-ketoalcohol of formula II would be a major advance in the art of providing 1α-hydroxylated cholesterols as the ultimate precursors of 1α-hydroxylated cholecalciferols. The present invention describes such a process for the preparation of 1α-hydroxylated cholecalciferols.

DETAILED DESCRIPTION OF THE INVENTION

The present invention relates to a novel method of synthesizing 1α-hydroxylated cholesterols avoiding the use of difficulty available and hazardous reagents and the formation of labile intermediates, readily adaptable for pilot plant scale operation. More particularly, the present invention relates to synthesis of 1α-hydroxycholesterols and its 25-hydroxy derivative comprising the steps of reducing the 3-keto group of 1α,2α-epoxy-6β-lower-alkyl(or aryl)sulfonyloxy-5α-cholestan-3-one and its 25-hydroxy derivative to form 1α,2α-epoxy-6β-lower-alkyl-(or aryl)sulfonyloxy-5α-cholestan-3-ol and its 25-hydroxy derivative, reductively cleaving 1α,2α-6β-lower-alkyl(or aryl)sulfonyloxy-5α-cholestan-3-ol and its 25-hydroxy derivative to form 1α-hydroxy-6β-lower-alkyl(or aryl)sulfonyloxy-5α-cholestan-3-ol and its 25-hydroxy derivative and eliminating lower-alkyl-(or aryl)sulfonic acid from 1α-hydroxy-6β-lower-alkyl(or aryl)sulfonyloxy-5α-cholestan-3-ol and its 25-hydroxy derivative to form 1α-hydroxycholesterol and its 25-hydroxy derivative, in which the reductive cleavage and reduction steps are regiospecific and stereospecific, respectively.

In the formulas presented herein, the various substituents are illustrated as joined to the steroid nucleus by one of three notations: a solid line (—) indicating a substituent which is in the β-orientation (i.e., above the plane of the molecule), a dotted line (---) indicating a substituent which is in the α-orientation (i.e., below the plane of the molecule), or a wavy line (∿) indicating a substituent which may be in the α- or β-orientation or may be a mixture of both forms. The formulas have all been drawn to show the compounds in their absolute stereochemical configuration. Inasmuch as the starting materials, as well as the final products, are derived from naturally occurring materials, they exist in the single absolute configuration depicted herein. However, the process of the present invention is intended to apply as well to the synthesis of steroids of the racemic series. Thus, one may begin the synthesis utilizing racemic starting material to prepare racemic product. Optically active product can be prepared by optical resolution of racemic product or of an intermediate utilized in the preparation thereof, as hereinafter described, by standard resolution techniques well known in the art, for example, involving fractional crystallization of diastereomeric salts.

As used throughout the specification and appended claims, the term "alkyl" denotes a straight or branched saturated hydrocarbon radical such as, for example, methyl, ethyl, 2-propyl, 1,1-dimethylethyl, hexyl and octyl, derived by abstraction of a proton from an alkane. The term "alkanol" denotes an alcohol such as, for example, methanol, ethanol, 2-propanol, 1,1-dimethylethanol, hexanol and octanol, derived by replacement of a proton of an alkane with a hydroxyl radical. The term "alkoxy" denotes a radical such as methoxy, ethoxy, 2-propoxy, 1,1-dimethylethoxy, hexoxy and octoxy, derived by abstraction of the hydroxylic proton of an alkanol. The term "aryl" denotes naphthyl, phenyl or phenyl substituted by one or more lower alkyl, lower alkoxy or halo (fluoro, bromo, chloro, iodo) groups such as, for example, 4-methylphenyl, 2,4-dimethylphenyl, 4-methoxyphenyl, 2,3-dimethoxyphenyl, 4-chlorophenyl and 2,4-dichlorophenyl. The term "lower" refers to the numerical range of 1 to 8.

The process of the present invention for the preparation of 1α-hydroxylated cholesterols of formula V is illustrated in Reaction Scheme II.

In the first step of the process, the 3-keto group of a 1α,2α-epoxycholestan-3-one of formula VI, the preparation of which is reported by Iacobelli, et al. in U.S. Pat. No. 3,887,545, is selectively reduced with diborane to afford a 1α,2α-epoxycholestan-3-ol of formula VII. The reduction is generally performed in an ethereal solvent, such as 1,2-dimethoxyethane, bis-(2-methoxyethyl)ether, dioxane, tetrahydrofuran and the like, at a reaction temperature of about −30° to about +30° C, most preferably at about 0° C. The relative molar amounts of the reactants are not narrowly critical as long as the theoretical amount of the reducing agent is employed. About 1 to 8 molarequivalents of diborane to equivalents is most preferred. Diborane-tetrahydrofuran complex is the preferred reducing agent.

ketone of formula VI is preferred. About 4 molar-

REACTION SCHEME I

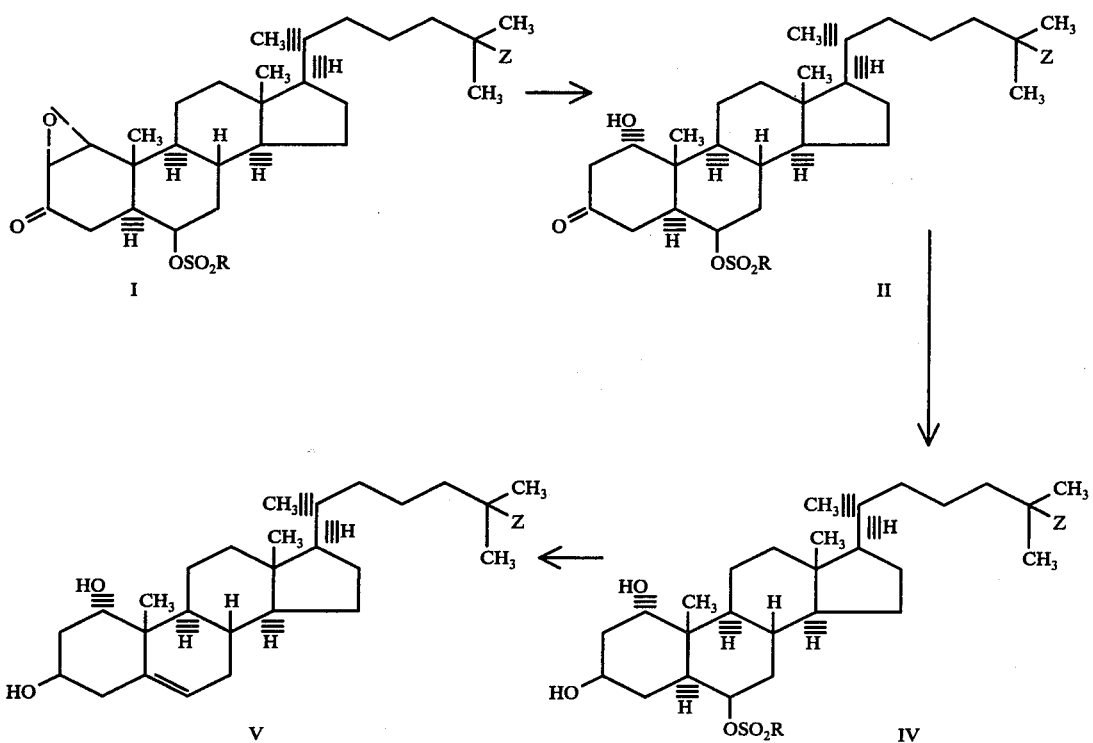

R is lower alkyl or aryl and Z is hydrogen or hydroxyl.

REACTION SCHEME II

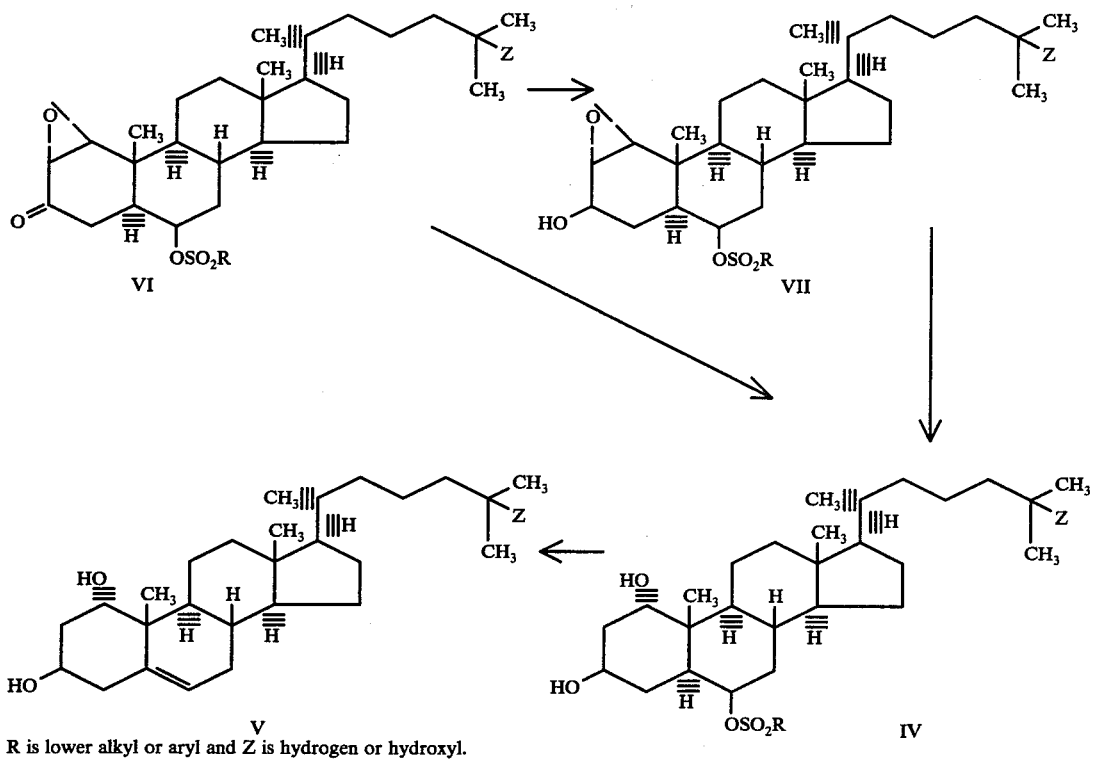

R is lower alkyl or aryl and Z is hydrogen or hydroxyl.

In the next step of the process sequence, the epoxy function of a 1α,2α-cholestan-3-ol of formula VII is reductively cleaved to afford a 1α-hydroxycholestan-3-ol of formula IV. The regiospecific reductive cleavage is accomplished by diborane in the presence of an alkali metal borohydride, such as sodium borohydride, potassium borohydride, lithium borohydride and the like, in an inert organic solvent. Suitable inert organic solvents include aromatic hydrocarbons, such as benzene, toluene and the like, ethereal solvents, such as 1,2-dimethoxyethane, bis-(2-methoxyethyl)ether, dioxane, tetrahydrofuran and the like, lower alkanols, such as methanol, ethanol, 2-propanol and the like, and acetonitrile. Ethereal solvents are preferred. Tetrahydrofuran is most preferred. While the reaction temperature range is not narrowly critical, it is preferred to perform the reductive cleavage within the range of about −30° to about +30° C, a reaction temperature of about 0° C being preferred. The relative molar amounts of the epoxyalcohol of formula VII and the reducing agents, diborane and alkali metal borohydride, are also not narrowly critical, as long as at least the theoretical amount of diborane and a catalytic amount of alkali metal borohydride is utilized. About 1 to 8 molar-equivalents of diborane to epoxy-alcohol of formula IV is preferred, 4 molar-equivalents being most preferred. About 1 to 10 molar-equivalents of alkali metal borohydride to epoxyalcohol of formula IV is preferred, 4 molar-equivalents of the alkali metal borohydride being most preferred. Diborane-tetrahydrofuran and lithium borohydride are the preferred reducing agents.

In the final step of the present reaction sequence, the sulfonyloxy group situated at the 6-position is eliminated to afford a 1α-hydroxycholesterol of formula V following the procedure described by Iacobelli, et al. in U.S. Pat. No. 3,887,545, utilizing lithium carbonate suspended in dimethylformamide.

While the process of the present invention for the preparation of 1α-hydroxylated cholesterols may be carried out stepwise as delineated in Reaction Scheme II and the immediately preceding description, the process is advantageously performed on a commercial scale without isolation of the intermediate epoxy-alcohol of formula VII, i.e., as a one-pot process.

1α-Hydroxycholesterol and the 25-hydroxy derivative thereof have been converted to 1α-hydroxycholecalciferol and 1α,25-dihydroxycholecalciferol, respectively, active metabolites of vitamin $D_3$. See D. H. R. Barton, et al., J. Am. Chem. Soc., 95, 2748 (1973) and M. R. Uskokovic', et al., U.S. Pat. No. 3,993,675, issued Nov. 23, 1976.

The following examples are for illustrative purposes only and are not to be construed as limiting the invention described herein in any way whatsoever.

EXAMPLE 1

1α,2α-Epoxy-25-hydroxy-6β-methylsulfonyloxy-5α-cholestan-3-ol

To 1-molar diborane-tetrahydrofuran complex (not stabilized with sodium borohydride, 157 ml) cooled in an ice bath, was added dropwise over about 25 minutes a solution of 1α,2α-epoxy-6β-methylsulfonyloxy-5α-cholestan-25-ol-3-one (20.0 g, 0.392 mole), in tetrahydrofuran (100 ml), with stirring under an atmosphere of nitrogen. After the addition was complete, the solution was stirred for about 25 minutes. Water was cautiously added to the reaction mixture cooled in an ice bath. The mixture was stirred for about 10 minutes and then evaporated at a bath temperature of 35° C in vacuo. The residue was partitioned between methylene chloride and water (ca. 1:1) and the organic layer was separated. The organic phase was washed with water, saturated sodium chloride solution, dried over anhydrous sodium sulfate and filtered. Evaporation of the filtrate gave 1α,2α-epoxy-25-hydroxy-6β-methylsulfonyloxy-5α-cholestan-3-ol, as a white foam.

EXAMPLE 2

1α,25-Dihydroxy-6β-methylsulfonyloxy-5α-cholestan-3-ol

To a mixture of 1-molar diborane-tetrahydrofuran complex (not stabilized with sodium borohydride, 157 ml) and lithium borohydride (3.4 g, 0.155 mole) cooled in an ice bath was added dropwise over about 25 minutes a solution of 1α,2α-epoxy-25-hydroxy-6β-methylsulfonyloxy-5α-cholestan-3-ol (20.0 g, 0.392 mole) in tetrahydrofuran (100 ml) with stirring under nitrogen. The suspension was stirred at 0° for about 6 hours, and then stored in a refrigerator (ca. 30° C) overnight. Water (200 ml) was added cautiously to the reaction mixture cooled in an ice bath. An additional 200 ml of water was added to the turbid solution and the solution was extracted with methylene chloride. The layers were separated and the organic phase was washed successively with water and saturated sodium chloride solution, dried over anhydrous sodium sulfate and filtered. Evaporation of the filtrate gave 22 g of 1α,25-dihydroxy-6β-methylsulfonyloxy-5α-cholestan-3-ol as a white foam.

EXAMPLE 3

1α,25-Dihydroxy-6β-methylsulfonyloxy-5α-cholestan-3-ol

To 1-molar diborane-tetrahydrofuran complex (not stabilized with sodium borohydride, 157 ml) cooled in an ice bath, was added dropwise over about 25 minutes a solution of 1α,2α-epoxy-6β-methylsulfonyloxy-5α-cholestan-25-ol-3-one (20.0 g, 0.392 mole), in tetrahydrofuran (100 ml) with stirring under an atmosphere of nitrogen. After the addition was complete, the solution was stirred for about 25 minutes. Lithium borohydride (3.40 g, 0.155 mole) was added in 1 portion to the reaction mixture, with stirring. The suspension was stirred in an ice bath for about 6 hours and then stored in a refrigerator (ca. 3° C) overnight. Water (200 ml) was added cautiously to the reaction mixture cooled in an ice bath. An additional 200 ml of water was added to the turbid solution and the solution was extracted with methylene chloride. The layers were separated and the organic phase was washed successively with water and saturated sodium chloride solution, dried over anhydrous sodium sulfate and filtered. Evaporation of the filtrate gave 22 g of 1α,25-dihydroxy-6β-methylsulfonyloxy-5α-cholestan-3-ol as a white foam.

We claim:

1. A process for the preparation of a compound of the formula

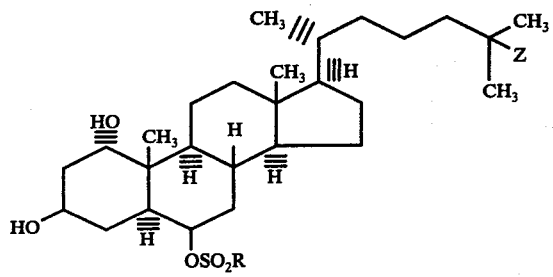

wherein R is lower alkyl or aryl and Z is hydrogen or hydroxyl and the 3-α-hydroxyl epimer thereof, which comprises the steps of (a) contacting a compound of the formula

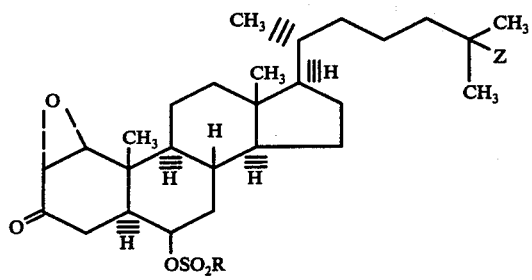

wherein R and Z are as above with diborane in an ethereal solvent selected from the group consisting of 1,2-dimethoxyethane, bis-(2-methoxyethyl)ether, dioxane and tetrahydrofuran at a temperature of −30° to +30° C to afford a compound of the formula

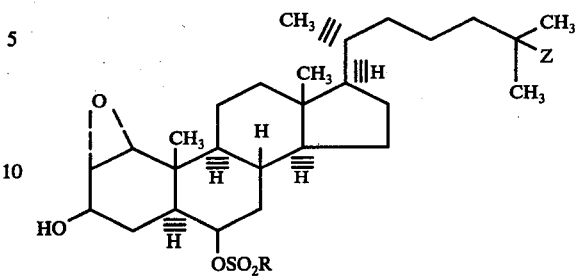

wherein R and Z are as above and the 3-α-hydroxy epimer thereof and b. contacting the above-obtained compound with diborane in the presence of an alkali metal borohydride in an ethereal solvent selected from the group consisting of 1,2-dimethoxyethane, bis-(2-methoxyethyl)ether, dioxane and tetrahydrofuran at a temperature of −30° to +30° C.

2. The process of claim 1 wherein Z is hydroxyl.
3. The process of claim 1 wherein R is lower alkyl.
4. The process of claim 1 wherein Z is hydroxyl and R is methyl.
5. The process of claim 1 wherein the ethereal solvent is tetrahydrofuran.
6. The process of claim 1 wherein the alkali metal hydride is lithium borohydride.
7. The process of claim 1 wherein the ethereal solvent is tetrahydrofuran.
8. The process of claim 1 wherein steps (a) and (b) are performed in one reaction vessel without isolation of the product formed in step (a).

* * * * *